United States Patent [19]

Selwyn et al.

[11] Patent Number: 5,225,888
[45] Date of Patent: Jul. 6, 1993

[54] PLASMA CONSTITUENT ANALYSIS BY INTERFEROMETRIC TECHNIQUES

[75] Inventors: Gary S. Selwyn, Hopewell Junction; Robert E. Walkup, Ossining, both of N.Y.

[73] Assignee: International Business Machines Corporation, Armonk, N.Y.

[21] Appl. No.: 633,811

[22] Filed: Dec. 26, 1990

[51] Int. Cl.$^5$ .............................................. G01B 9/02
[52] U.S. Cl. ...................................... 356/346; 356/352
[58] Field of Search ...................... 356/346, 352, 351; 250/339, 343, 227.29; 359/578; 156/626

[56] References Cited

U.S. PATENT DOCUMENTS

| | | | |
|---|---|---|---|
| 3,740,144 | 6/1973 | Walker | 359/578 |
| 3,914,055 | 10/1975 | Wolga et al. | 356/301 |
| 4,005,937 | 2/1977 | Barrett | 356/352 |
| 4,035,643 | 7/1977 | Barrett | 356/346 |
| 4,092,070 | 5/1978 | Smithline | 356/352 |
| 4,204,771 | 5/1980 | Schull et al. | 356/346 |
| 4,448,486 | 5/1984 | Evans | 356/352 |
| 4,454,001 | 6/1984 | Sternhelm | 156/626 |
| 4,482,248 | 11/1984 | Papuchon et al. | 356/346 |
| 4,525,067 | 6/1985 | Hernandez | 356/346 |
| 4,602,981 | 7/1986 | Chen et al. | 156/627 |
| 4,675,072 | 6/1987 | Bennett et al. | 156/626 |
| 4,680,084 | 7/1987 | Helmann et al. | 156/626 |
| 4,711,573 | 12/1987 | Wijnges | 356/346 |
| 4,717,446 | 1/1988 | Nagy | 156/626 |
| 4,732,480 | 3/1988 | Fortunato et al. | 356/351 |
| 4,735,507 | 4/1988 | Crane, Jr. et al. | 356/352 |
| 4,743,114 | 5/1988 | Crane, Jr. | 356/352 |
| 4,758,304 | 7/1988 | McNeil et al. | 156/626 |
| 4,838,694 | 6/1989 | Betz et al. | 356/357 |
| 4,999,013 | 3/1991 | Zoechbauer et al. | 356/346 |
| 5,059,784 | 10/1991 | Northrup | 250/227.29 |

Primary Examiner—Samuel A. Turner
Attorney, Agent, or Firm—Whitham & Marhoefer

[57] ABSTRACT

An interferometer (18 or 40) is used to identify trace constituents in a plasma during processing semiconductor devices such as transistors. Light emissions collected from the processing chamber (10) are collimated by lens (14) and transmitted to the interferometer (18 or 40) which selectively allows therethrough particular wavelengths of light which are characteristic of the excitation emissions of certain atoms such as sodium and copper. The light intensity at the selected wavelengths is sensed by a photomultiplier tube (30). In one embodiment, the interferometer (18) is a Fabry-Perot type interferometer and the separation of the plates (20 and 22) which form the Fabry-Perot etalon is controlled using a piezoelectric driver (26). A signal processor (34) correlates the sensed light emissions from the photomultiplier tube (30) with the selected wavelength that is determined by the piezoelectric driver (26). In another embodiment, the interferometer (40) is a narrow bandpass interferometric filter which is tiltable with respect to the collimated incident light from the processing chamber (10). Tilting a narrow bandpass interferometric filter (42) with respect to incident light changes the path length through the filter (42) and allows for the selective transmission of certain wavelengths of light. By rapidly tilting the narrow bandpass interferometric filter (42) at a rate between 5-300 Hz with respect to the incident light, a narrow range of wavelengths on the order of 3 nm can be scanned.

6 Claims, 3 Drawing Sheets

PLASMA CONSTITUENT ANALYSIS BY INTERFEROMETRIC TECHNIQUES

BACKGROUND OF THE INVENTION

1. Field of the Invention

The present invention generally relates to solid state device manufacturing and, more particularly, to an interferometric optical emission detection system used for trace constituent contamination monitoring and endpoint detection.

2. Description of the Prior Art

Sodium (Na) and other alkali metals are unwanted impurities which adversely affect the operation of transistors and other solid state devices. Sodium is a mobile ion and will cause the gate of a transistor to turn on and off at different voltages. Variable operation of the gate will, in turn, cause inconsistent operation of other devices such as memory chips and the like. Sodium contamination of transistors can result from human contact with chemicals and tools used in device manufacturing (i.e., sodium ions can be transported from a person's body onto a processing tool simply by the person touching the tool), impurities present in processing reagents such as photoresist, from the manufacture and storage of these processing reagents, by the sodium which is naturally present in the atmosphere corrupting the processing plant environment (i.e., fog, mist, and rainwater seepage can carry sodium ions from the atmosphere into a processing plant), or by other means. Field Effect Transistors (FETs) are four orders of magnitude more sensitive to alkali metals than bipolars; therefore, sodium contamination is a particular concern in FET processing.

Sodium emission, as well as other trace constituent emissions, can be detected optically. Most of today's optical emission detecting systems used in transistor processing can be categorized as either monochromators with photodiode array detectors or as scanning monochromators with a photomultiplier detector. These types of optical emission systems are available from the following companies: Tracor-Northern, Plasma-Therm Analytical, Xenix, and EG&G PAR. One problem with these types of optical emission systems is that they offer low resolution detection; often greater than 1 nm and sometimes as poor as 10-20 nm. Low resolution detection results in insufficient wavelength dispersion and convolution of the desired emission signal with unwanted background and other emissive interferences. Because of this, low resolution detection also provides low sensitivity for trace species detection against the intense background emission of plasma processing tools. This is further compounded by low light throughput which is typical of conventional monochromators.

As a result of the low sensitivity of conventional optical emission systems, the usual method used for detecting sodium impurities in FETs is by electrical measurement at the end of the chip fabrication process. Clearly, it would be advantageous to have some means which is sensitive enough to detect trace levels of an impurity such as sodium ion before a large number of chips have been damaged. Ideally, potential processing problems could be identified when unacceptable levels of sodium are detected during the fabrication of FETs, and the processing could be halted temporarily to clean the tools and/or check the sodium levels in the processing reagents.

Proper etching endpoint detection is also a major concern in transistor manufacturing. One prior art method of determining the endpoint of material removal is simply timing the etch process according to the rate of material removal. To use a timed etch procedure, it is necessary to empirically determine the time at which all of the desired material has been removed, but the underlying layer has not been etched significantly. Timing is not an ideal procedure for determining the proper etching endpoint because it is indirect and the consequences of improper etching are significant. Underetching will cause a degradation of the gain of the transistor, while overetching will result in a degraded contact between the intrinsic and extrinsic base regions.

Optical emission detection has been proposed as a means for detecting the endpoint at which an etching operation should be halted. A monochromator or bandpass filter can be used to select wavelengths of light at which a desired optical emission will occur. High spectral resolution is always preferable to low spectral resolution for monitoring and analysis of plasma species because, with sufficiently high resolution, it is possible to minimize interference from other emitting plasma species. Moreover, if light throughput is held constant, peak height will increase relative to the background as spectral resolution is improved. Accordingly, high spectral resolution can provide considerable advantages in sensitivity for etch endpoint detection and in the identification of weakly emitting plasma species such as in sodium ion contaminant analysis. Unfortunately, the usual methods for obtaining high spectral resolution, e.g., narrowing monochromator slits or utilizing larger monochromators, have practical limits for use in transistor manufacturing applications. When the slits of a monochromator are narrowed, higher resolution is achieved; however, the light throughput is significantly reduced and, thus, the overall sensitivity is reduced. Using larger monochromators is unacceptable because they would require costly clean room space and are generally impractical for manufacturing applications.

Laser-induced fluorescence (LIF) is a newer technique used in transistor manufacturing for identifying trench etch endpoints and can be used to identify trace constituents. For example, U.S. Pat. 4,675,072 to Bennett et al. discloses an LIF system used to detect and control the reactive ion etch (RIE) through of a given layer in a wafer by detecting a large change in the concentration of a selected minor species from the wafer in the etching plasma. Although LIF is generally used for monitoring major species, LIF may be used to detect trace Na ion contaminants during etching; however, Na only fluoresces at the excitation wavelength of 588.996 nm or 589.593 nm and since scattered laser light is a severe limitation on the sensitivity of LIF, the presence of Na may not be easily detected because of unavoidable interference from scattered laser light off the tool walls and windows. Furthermore, methods to reduce scattered laser light, such as the use of Brewster angle windows and light baffles, are impractical for use on commercial etch tools. LIF may also be used to detect trace copper atoms which appear in aluminized lines as a means to detect an etch endpoint. However, copper atoms will exhibit fluorescence at 324.775 nm which is a wavelength that would require frequency doubling of the dye laser; a process generally regarded as infeasible for manufacturing applications because more powerful lasers are required for this task and a skilled laser operator would be required.

Several laser interferometer techniques are now in standard practice for optically detecting line widths and etch endpoints. U.S. Pat. No. 4,454,001 to Sternheim et al. and U.S. Pat. No. 4,680,084 to Heimann et al. are directed to etch monitoring using laser interferometric methods whereby the thickness of the region being etched is simultaneously monitored. U.S. Pat. No. 4,838,694 to Betz et al. discloses a laser interferometry process which uses the reflected laser beam. U.S. Pat. No. 4,717,446 to Nagy et al. discloses a method, using a monitor wafer which is correlated to the endpoints of the working wafer, for detecting the endpoint of the etch of an epitaxially grown silicon whereby a laser is used to measure the etch rate of the monitor wafer by measuring the reflected light off the oxide layer. U.S. Pat. No. 4,602,981 to Chen et al. is directed an impedance monitoring technique for plasma etching wherein endpoints are detected by an impedance change of the plasma; however, the Chen et al. reference does disclose that laser interferometry is well established in the art and points out that the laser measures the thickness of the film removed as the etch process proceeds. U.S. Pat. No. 4,758,304 to McNeil et al. discloses an apparatus for air ion etching which utilizes an interferometer for surface monitoring. The methods described in Chen et al. and McNeil et al. are generally insensitive to the precise wavelength of the detected light. Before the invention thereof by the applicants, interferometers have not been used in solid state device manufacturing for detecting trace emitting species in a complex background spectra.

Furthermore, several techniques for controlling interferometers are now in common practice. U.S. Pat. No. 4,482,248 to Papuchon et al. discloses an interferometer used for optical filtering. U.S. Pat. No. 4,711,573 to Wijntjes et al. discloses a dynamic mirror alignment control which utilizes an interferogram for analyzing sample materials wherein a closed loop servo motor is used to maintain position orientation. U.S. Pat. No. 4,448,486 to Evans discloses the use of mirrors in a Fabry-Perot interferometer used to change the bandwidth of the Fabry-Perot interferometer. The applicants invention describes completely new methods for using and controlling interferometers in transistor manufacturing.

SUMMARY OF THE INVENTION

It is therefore an object of the present invention to provide methods of using light wave interferometry for the detection of trace plasma species.

It is another object of this invention to overcome the low light throughput and corresponding low resolution disadvantages of using a monochromator for wavelength selection to monitor optical emissions of trace plasma species.

It is yet another object of this invention to describe a new, low-cost, durable optical emission detection system which operates using interferometric principles.

According to the invention, light wave interferometry is used in solid state device manufacturing processes to identify trace plasma species. By using light wave interferometry, high resolution optical emission detection is achieved without the use of a monochromator. The light wave interferometry methods of the present invention result in a high light throughput efficiency, high spectral resolution, and an associated improvement in detection sensitivity and selectivity. The light wave interferometry methods of the present invention are useful in etch endpoint analysis and in the identification of important trace contaminants such as sodium impurities encountered during FET fabrication.

One method involves the use of a Fabry-Perot interferometer and relies upon the constructive and destructive interferences of entering light between two highly reflective parallel plates separated by a known distance of air. As discussed by R. P. Feynman et al. in *The Feynman Lectures on Physics*, Vol. III, Addison-Wesley, Reading, Mass., pp. 4–10, 1965, an interferometer operates on the principle of maintaining a standing wave between two reflective plates. The standing wave criterion will be met when, $k_f=j\pi/L$, where $k_f$ is the wavenumber ($k=2\pi/\lambda$) of the jth mode (j=any integer) and L is the separation of plates. By varying the separation between the two plates, which can be accomplished with a piezoelectric drive or similar means, the transmitted light may be tuned with very high resolution (e.g., 0.001 to 0.08 nm) over a narrow wavelength range. Such a system can typically transmit 70% of the light at the selected wavelength which compares very favorably with monochromator systems that have lower resolution and transmit only 5–10% of the light. Since multiple orders are also transmitted by the air-spaced etalon, it is also necessary to use prefilters to block out multiple order transmission.

Air-spaced Fabry-Perot interferometers are commercially available and have been primarily used in transistor and other solid state device manufacturing for linewidth measurements of major emitting species. For example, R. Walkup et al. disclosed the use of air spaced Fabry-Perot interferometers for linewidth measurements in *J. Chem. Phys.*, 84, 2668 (1986). In contrast to prior uses of Fabry-Perot interferometers in solid state device manufacturing, the present invention anticipates the use of a Fabry-Perot etalon for end point detection and for the selective detection of trace emitting species from a complex background spectra. The present invention's use of the Fabry-Perot interferometer takes advantage of the high light throughput which occurs with the Fabry-Perot interferometer which is not present in other means of optical emission detection (e.g., monochromators). High light throughput provides no major advantage in line width analysis because a major plasma species, as opposed to a trace species, is usually being monitored during line width analysis.

Another method by which light wave interferometry can be used to monitor trace species during transistor manufacturing is to use a tiltable narrow bandpass interference filter to scan a small range of wavelengths. Narrow bandpass interference filters are commercially available from Oriel Optics, Andover Corp., Spindler, and Hoya and include a series of thin dielectric layers which are used to produce constructive or destructive interference of the incident light. Narrow bandpass interference filters are similar to the air spaced Fabry-Perot etalon in principle; however, the separation between layers in a narrow bandpass interference filter is fixed and several dielectric layers are used instead of air. While the resolution of a narrow bandpass interference filter is typically somewhat lower than with a Fabry-Perot interferometer, multiple order transmission problems associated with Fabry-Perot interferometers are not present when a narrow bandpass interference filter is used. This is because a Fabry-Perot interferometer operates in a single reflective cavity and, narrow bandpass interference filters operate by multiple reflections between successive dielectric layers. In this way, sensitivity to mode effects is minimized. Narrow bandpass interference filters have been widely used in materials processing plasmas for endpoint detection. In fact, some commercial reactors come equipped with specific bandpass interference filters, such as the Zylin metal etch reactor which is equipped with a 10 nm bandpass filter for aluminum (Al) atom detection. Harshberger et al. have described a reactor equipped with a bandpass interference filter in *J. Electronic Materials*, 7, 429 (1978). Interference filters are typically used in the same way as low resolution optical spectrometers for etch endpoint detection. The high light throughput of these filters provides an advantage over a fixed wavelength monochromator, and also has a lower capital cost and greater reliability than a monochromator. However, the fixed wavelength selection of the filter makes these light detection systems vulnerable to errors resulting from unwanted detection of interferences within the transmission range of the filter. The absolute emission intensity measured by the bandpass filter also includes intensity from the underlying continuous emission of the plasma. This continuous emission can be significant and can dominate over weak, wavelength-specific emission from trace or impurity plasma species. The continuum can result from electron-ion recombination or changes in the electron energy distribution in the plasma. Fixed wavelength detection using filters means that the desired emission may be indistinguishable from other emissions in the plasma.

Figure 1:
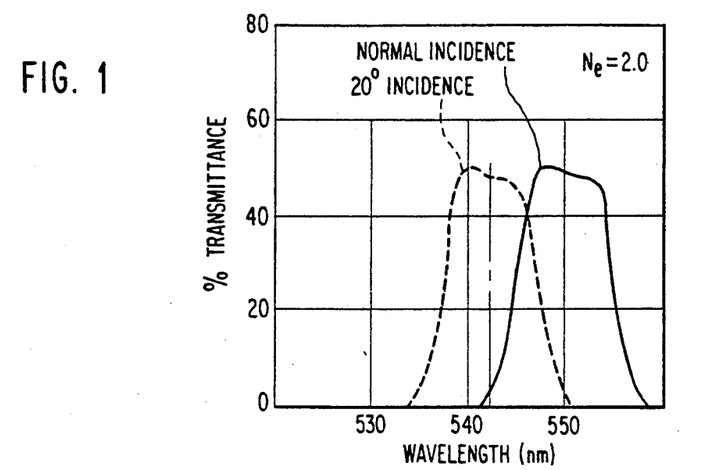
FIG. 1 is a graph showing the bandpass shifting towards a shorter wavelength when the angle of incidence of collimated light on the bandpass interferometric filter moves away from normal.
Figure 2:
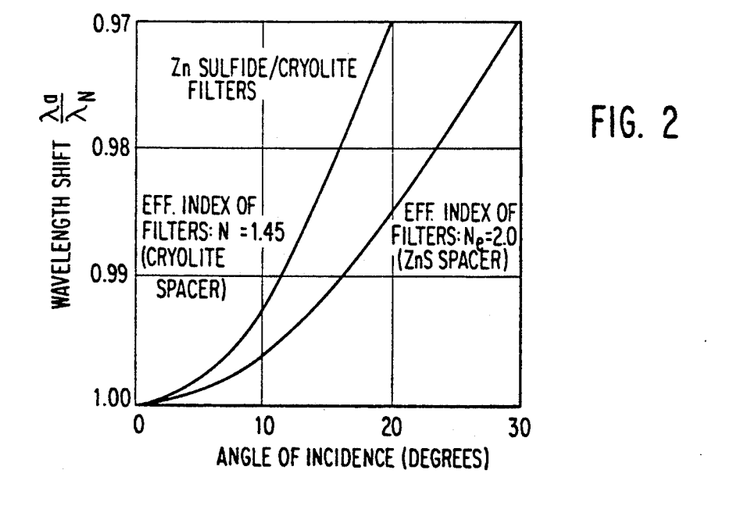
FIG. 2 is a graph showing the calculated percentage of wavelength shifting which occurs as the angle of incidence of collimated light changes for two different bandpass interferometric filters.

It is known that bandpass interferometric filters can be tuned to shorter wavelengths by tilting the filter with respect to the incident light. Tilting the filter effectively changes the path length of the light between the dielectric layers without changing the layer separation or composition (as pointed out above, the distance between layers is fixed). Hence, the transmission peak of a given bandpass interferometric filter can be tuned slightly to shorter wavelengths by tilting the filter to an appropriate orientation. FIGS. 1 and 2, which are taken from the Oriel Optics catalog of 1986, illustrate the effect of varying the angle of incidence of a collimated beam on bandpass interferometric filter. FIG. 1 shows that if the angle of incidence is increased, the peak wavelength is shifted to shorter wavelengths. This shift is due to the fact that the path difference between the direct transmitted beam and the beam formed by the multiple reflection decreases. The angle shift in peak wavelength can be estimated for angles less than thirty degrees using equation 1:

$$\frac{\lambda_a}{\lambda_o} = \frac{\sqrt{N_e^2 - \sin^2 a}}{N_e^2}$$

where:
  a is the angle of incidence,
  $\lambda_a$ is the peak wavelength at angle a,
  $\lambda_o$ is the peak wavelength at normal incidence, and
  $N_e$ is the incidence angle shift factor or the "effective index of refraction" of the filter.

$N_e$ is not the actual refractive index of the spacer layer, rather it is dependent on both the high and low index materials in the filter. Oriel Optics experimentally determined that $N_e$ in a zinc sulfide/cryolite system is 1.45 for a cryolite spacer layer and 2.0 for a zinc sulfide spacer layer. FIG. 2 plots the approximate wavelength shift versus the angle of incidence, as calculated according to equation 1, for two bandpass interferometric filters which each include a sulfide/cryolite system and where one uses a cryolite spacer layer and the other uses a zinc sulfide spacer layer. For small angles (e.g., under 30 degrees), the shape of the band pass does not change appreciably except for a small reduction in transmission. However, at larger angles band pass shape becomes highly distorted. For 5 nm and 10 nm filters, shifting by about 10 nm without drastic change in the band pass shape can be achieved.

Narrow and very narrow bandpass interference filters are a subset of bandpass interferometric filters and include filters having a full-width half maximum (FHWM) ranging between 0.1 nm and 1 nm. The distinctions between bandpass interferometric filters, narrow bandpass filters, and very narrow bandpass interference filters are qualitative. The FHWM refers to the error in wavelength detection measured at one half the peak height. Narrow bandpass interference filters are available from the Andover Corp. of Massachusetts as well as other vendors. Narrow bandpass interference filters show a critical dependence on filter orientation to collimated incident light. For example, if a very narrow bandpass interference filter having an FHWM=0.2 nm varied by 5° from normal incidence, an approximately 1 nm shift in peak wavelength will occur without significant broadening of the transmission curve. Hence, unlike 5 nm and 10 nm bandpass interferometric filters which shift about 10 nm without drastic change in band pass shape, very narrow bandpass interference filters have considerably less range, but have improved spectral resolution over that range.

Figure 3:
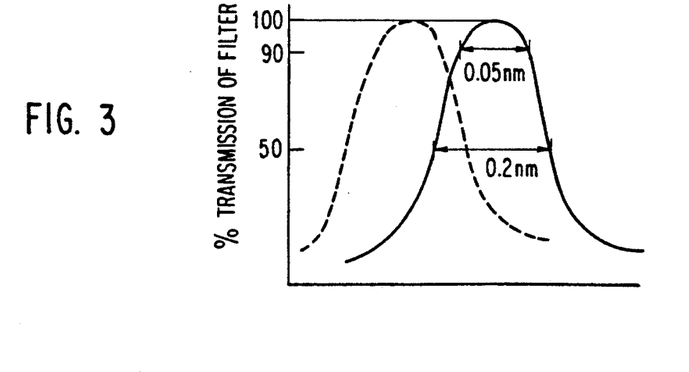
FIG. 3 is a graph showing a plot of the transmission of light versus wavelength when the narrow bandpass interference filter is perpendicular and angularly oriented with respect to the incidence of light.

The present invention uses the "problem" of angular dependent wavelength shifts with narrow bandpass filters as a means to greatly improve optical emission detection sensitivity. Specifically, the invention contemplates mounting a narrow bandpass filter in a holder which can be rapidly tilted with respect to the collimated light collected from a plasma reactor. By tilting the bandpass filter 5°, an approximate range of 1 nm can be scanned with a bandpass of better than 0.2 nm at the half height or 0.05 nm at 90% transmission maximum. FIG. 3 shows a plot of the transmission of the filter versus wavelength where the bandpass is 0.2 nm at the half height and 0.05 nm at 90% transmission and shows how the plot shifts as the narrow bandpass filter is tilted. A photomultiplier tube is used to detect the transmitted light through the tilting narrow bandpass filter. The output from the photomultiplier tube is sent to an oscilloscope or lock-in amplifier which is synchronized with filter movement. Therefore, the lock-in amplifier can sensitively measure a change in the photomultiplier signal as a function of filter orientation.

Since atomic emission lines are extremely sharp (e.g., on the order of 0.0001 nm) any atomic emission detected will show a very strong signal dependence on filter orientation. This dependency on filter orientation provides the advantage of effectively eliminating background emission noise (i.e., background emission is considered to be the emission which is relatively constant over the range of wavelengths scanned). Eliminating background emission enables the detection of very small signals on a large background. In the conventional method of using bandpass filters where the bandpass filter is fixed (i.e, it is not tilted as referenced above to Harshberger et al., *J. Electronic Materials*, 7, 429 (1978)), small signals could not be distinguished from a large background because both signal and background are continuously detected. In this wavelength specific detection technique, signal is distinguishable from background. Hence, background subtraction as well as high light throughput and high spectral resolution make the inventive means of optical emission detection wherein a narrow bandpass interference filter is rapidly tilted to achieve a scanning function a far superior means for monitoring plasmas than the conventional optical emission detection systems which use monochromators or fixed wavelength bandpass filters.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 4:
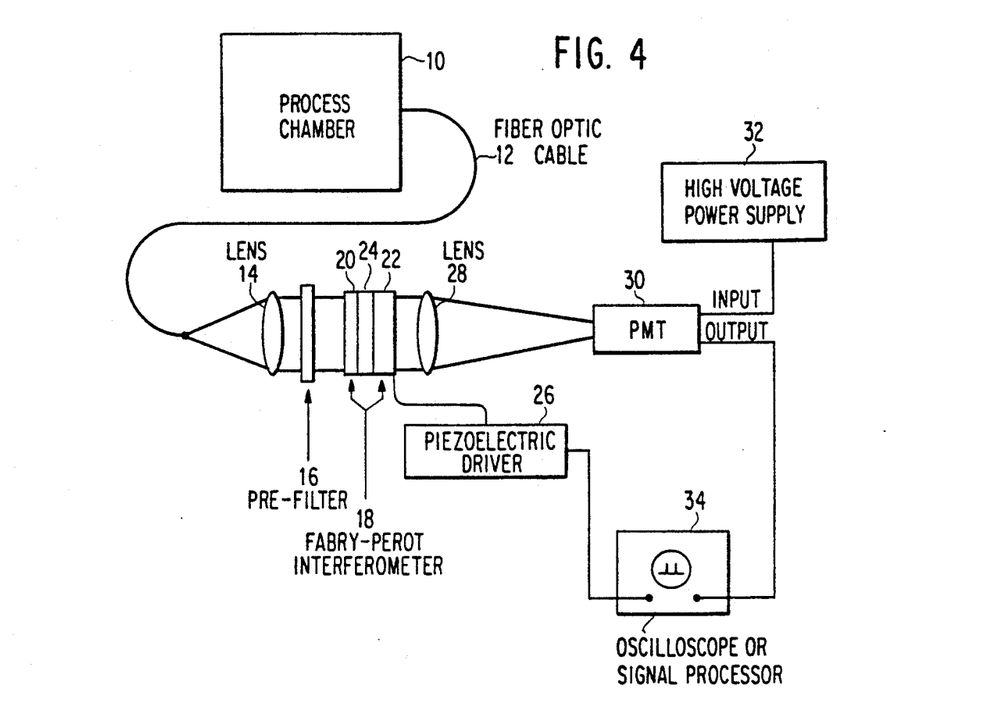
FIG. 4 is a schematic drawing showing a Fabry-Perot interferometer used to monitor a process chamber.

Referring now to the drawings, and more particularly to FIG. 4, there is shown a process chamber 10 wherein etching processes, such as reactive ion etching (RIE) and the like, performed in the fabrication of solid state devices such as transistors (not shown) are performed. A fiber optic cable 12 is used to collect light from the plasma chamber 10 and transport it to a collimating lens 14. It is anticipated that the fiber optic cable 12 could be eliminated and the collimating lens 14 alone could be used to both collect and collimate light emitted from a reactor window (not shown). It is also anticipated that more complex arrangements which may include multiple fiber optic cables, multiple lenses in series, apertures, and baffles, are likely to be used to collect and collimate light from the plasma chamber 10 since there are many different, well established, techniques for fulfilling these functions. Collimation, of course, can be achieved using a series of lenses where the distances between the optical fiber and each of the lenses are appropriately adjusted. The collimated light from lens 14 is passed through a pre-filter 16, or series of pre-filters, so that multiple order transmissions are blocked out. A narrow bandpass filter (approximately 1 nm) would be a suitable pre-filter 16 and would block many of the unwanted multiple orders that the Fabry-Perot interferometer 18 would otherwise pass. A monochromator could be substituted in place of pre-filter 16 for fulfilling the function of eliminating the transmission of multiple orders; however, if a monochromator were used, it should be set such that the percentage of light transmission through the monochromator is very high.

The filtered, collimated light is then transmitted to an air spaced Fabry-Perot interferometer 18. Fabry-Perot interferometers 18 are commercially available from a number of sources and typically comprise two glass plates with aluminum reflective coatings 20 and 22, respectively, separated by an air space or etalon 24. In order to tune the Fabry-Perot interferometer 18, a piezoelectric drive 26 or some other suitable means is used to vary the separation between the plates 20 and 22. The Burleigh company of Massachusetts makes a Fabry-Perot interferometer 18 which is combined with a piezoelectric drive 26. Using a very sensitive means to vary the separation between the plates 20 and 22 such as a piezoelectric drive 26 allows the transmitted light to be tuned with very high resolution (e.g., on the order of 0.001 to 0.08 nm) over a narrow wavelength range. The Fabry-Perot interferometer 18 is capable of transmitting seventy percent or more of the light at the selected wavelength, which compares very favorably relative to a monochromator which only transmits five to ten percent of the light at a selected wavelength and typically has lower resolution.

The light transmitted from the Fabry-Perot interferometer 18 is collected using lens 28 and sent to a photomultiplier tube 30 for sensing. It is anticipated that other sensing devices such as photodiodes and the like could be used instead of the photomultiplier tube 30 and that the desired sensitivity will dictate which light sensing arrangement is used. Photomultiplier tubes 30 are commercially available from RCA Electronics and EMI Electronics and require a high voltage input 32. The high voltage input 32 is used in the photomultiplier to achieve a high bias potential between successive electron amplification stages for greater detection sensitivity. Output from the photomultiplier tube 30 is sent to an oscilloscope 34 or other suitable signal processor. The wavelength transmission of the Fabry-Perot interferometer 18 varies with plate 20 and 22 separation and is synchronized by the piezoelectric driver 26. Hence, the oscilloscope 34 also receives output from the piezoelectric drive 26 so that the selected wavelength determined by the Fabry-Perot interferometer 18 can be correlated with the light sensed by the photomultiplier tube 30.

Hence, the arrangement shown in FIG. 4 allows an operator to rapidly determine the intensity of emission of a specific wavelength of light from all of light emissions within a specific wavelength range which occur in a processing chamber 10 while etching the solid state devices. Therefore, the presence of trace constituents such as sodium ion, which fluoresces only at the excitation wavelengths of 588.996 nm or 589.593 nm, can be detected by using the Fabry-Perot interferometer 18 to select these wavelengths and using the photomultiplier tube to sense if light is transmitted at these wavelengths. In a particular trace constituent confirmation scheme, the piezoelectric drive 26 drives the plates 20 and 22 to two different separations 24 so that emissions at both wavelengths can be detected and used as a confirmation of the presence of sodium. The continuous background emission is also distinguished from the wavelength specific sodium emission. In another use, the Fabry-Perot interferometer 18 can be used for etch endpoint detection where the interferometer 18 is used to detect copper atoms which are present in aluminized lines. During personalization, or the wiring and interconnection of multiple circuits on a microchip, oxide is etched until metallized lines containing aluminum (Al) that include 2-3% Copper (Cu) are exposed. Al cannot be easily used for endpoint detection because the counter electrode and chamber walls are sources of Al emissions; therefore, the Al from the line is not easily distinguishable from Al sputtered from the walls and electrode of the plasma processing tool. However, it is possible to use the small amounts of copper from the aluminum metallurgy to monitor etch endpoint because small via pattern factors (2-5%) and the small percentage concentration of Cu in the Al metallurgy (2-5%) result in a very low concentration of Cu in the plasma. Copper emission can be detected at 522.006 nm and 521.820 nm using the same concept described above for sodium detection, i.e., detecting emissions at the two wavelengths confirms the presence of copper.

Because the Fabry-Perot interferometer 18 allows a greater light transmission at the desired wavelength than a monochromator, the system shown in FIG. 4 has much greater sensitivity than convention optical emission systems. Moreover, the high spectral resolution of the Fabry-Perot interferometer 18 enables the optical system of FIG. 4 to take full advantage of the very narrow linewidth of atomic transitions which further aids in detection sensitivity and greatly reduces the likelihood of interference resulting from other plasma species emitting at wavelengths close to the desired wavelength. Scanning the Fabry-Perot interferometer 18 allows for the subtraction of background light and thereby, further, improves detection sensitivity. Also, since atomic emission doublets or triplets may be resolved, positive identification of a particular atomic species is possible. Monochromators, which often have lower resolution, tend to blur fine emission structure and, therefore, cannot be used to determine singlets from doublets.

Figure 5:
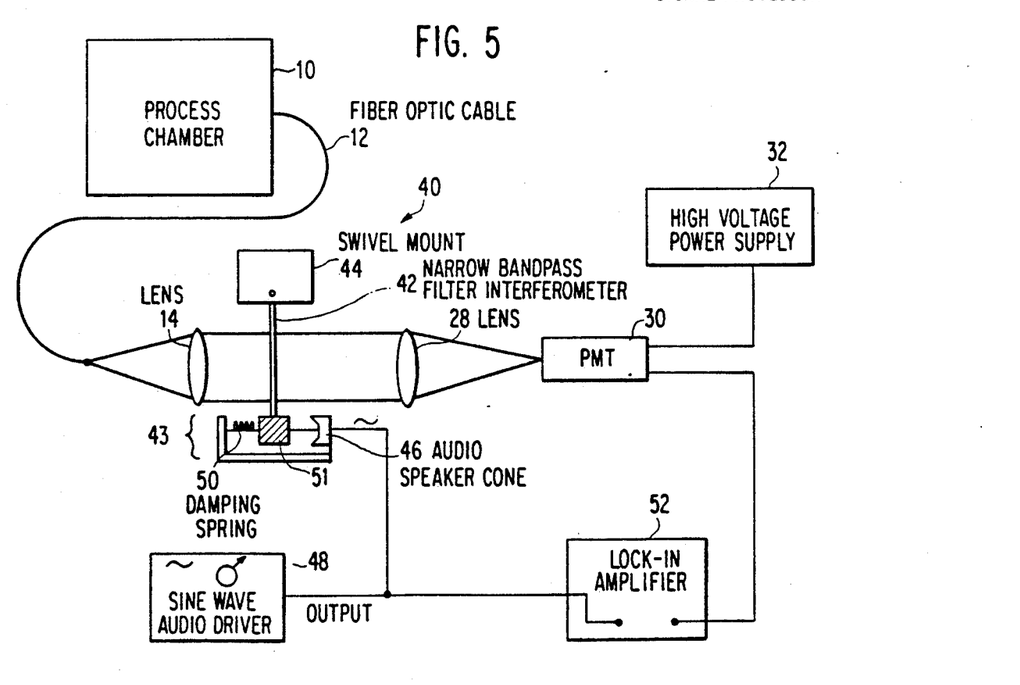
FIG. 5 is a schematic drawing showing a narrow bandpass interference filter used to monitor a process chamber.
Figure 6:
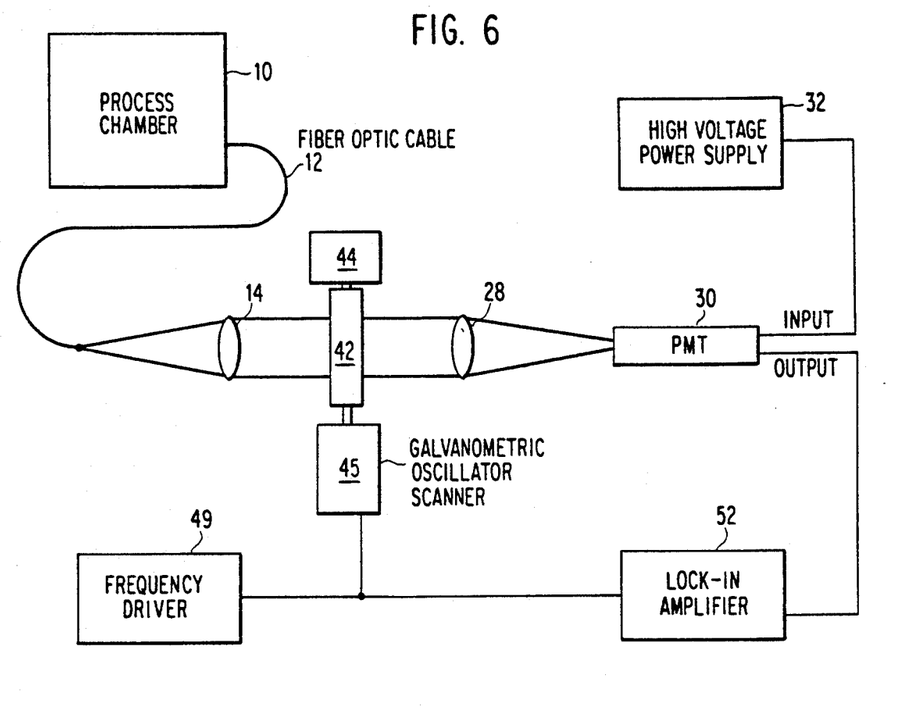
FIG. 6 is the same system shown in FIG. 5 except that a galvanometric oscillator is used for tilting the bandpass filter.

FIGS. 5 and 6 show alternative optical emission detecting sytems which utilize an interferometric technique for detecting the presence of trace constituents similar to that shown in FIG. 4. For example, a fiber optic cable 12 collects and transports light emissions from a processing chamber 10 in which an etching procedure or the like is being performed. A collimating lens 14 collimates the light from cable 12 and directs it towards an interferometer, shown generally as 40, which allows the high light throughput transmission of certain wavelengths of light. A lens 28 collects the emissions at the selected wavelengths and directs them into a photomultiplier tube 30 driven by a high voltage power supply 32. As described above in conjunction with FIG. 4, there can be several variations on the types of equipment used for collecting, collimating and sensing the light emissions during processing and all those variations are equally applicable with regard to FIGS. 5 and 6. The chief difference between the system shown in FIG. 4 and the systems shown in FIGS. 5 and 6 is the type of interferometric system 40 which is used for selecting the wavelengths of light or scanning through a small range of wavelengths.

FIGS. 5 and 6 show a narrow bandpass filter interferometer 42 is connected to a swivel mount 44 and is positioned in the path of the transmitted light. As pointed out above, narrow bandpass filters 42 are commercially available Andover Corp., Oriel Optics, Spindler, and Hoya, and are used for etch endpoint analysis in present day processing chambers 10. The present invention differs from the prior art in that the narrow bandpass filter interferometer 42 of the present invention is tiltable with respect to the collimated light from lens 14. The inventors have found that the phenomena of tuning a narrow bandpass filter interferometer 42 to shorter wavelengths, which results from tilting the filter with respect to incident light such that the path length of the light between the dielectric layers is changed (i.e., the angular-dependent wavelength shift discussed above), can be used as a means to improve optical emission detection sensitivity. Another advantage of the arrangement shown in FIGS. 5 and 6 is that pre-filters 16 are not required since multiple order transmissions are not a problem when a narrow bandpass filter interferometer 42 is used, unlike when a Fabry-Perot interferometer 18 is used.

FIGS. 5 and 6 show the narrow bandpass filter interferometer 42 is connected at its lower portion to angle unit 43 or galvanometric oscillator 45, respectively; however, it is anticipated that any configuration for mounting the narrow bandpass filter interferometer 42 such that it can be rapidly tilted with respect to the collimated light from lens 14 will be within the scope of the present invention. In a preferred embodiment, the narrow bandpass filter interferometer 42 has an FHWM on the order of 0.2 nm. Any device that responds in a smooth reproducible manner can be used to angularly drive the narrow bandpass filter interferometer 42. For example, a speaker cone 46 as shown in FIG. 5, a piezoelectric drive (not shown), or a galvanometric scanner shown in FIG. 6 can be used for tilting the narrow bandpass filter interferometer 42.

In the configuration shown in FIG. 5, a speaker cone 46, which responds very smoothly to a sine wave, is driven by the output of a sine wave audio driver 48 to rapidly tilt the narrow bandpass filter interferometer 42 reproducibly in phase with the audio frequency sine wave. Undesired motion of the narrow bandpass filter interferometer 42 can be dampened using a spring 50 connected to a weight 51 at the base of said narrow bandpass filter interferometer 42 or by adding other suitable frictional inhibitors to the phase tilt unit 44.

In the preferred configuration shown in FIG. 6, the narrow bandpass filter interferometer 42 is rapidly tilted at a frequency ranging between 5 and 300 Hz by means of connection to a galvanometric oscillator scanner 45 such as the G320 scanner available from General Scanning of Watertown, Mass. The scanner 45 is driven by a sinusoidal frequency supply 49. This tilts the narrow bandpass filter interferometer 42 with respect to the incident light collected from the processing chamber 10 so that the narrow bandpass filter interferometer 42 can be made to scan approximately a 3 nm range of wavelengths with a bandpass better than 0.2 nm at the half height or 0.05 nm at 90% transmission maximum. Closed loop galvanometric scanners 45 are now available so that the angular motion of the filter 42 is highly accurate and reproducible. Output signals from the sine wave audio driver 48 shown in FIG. 5 or the sinusoidal frequency driver 49 shown in FIG. 6 and from the photomultiplier tube 30 are sent to a lock-in amplifier 52. Lock-in amplifiers are commercially available from Stanford Research Instruments and EG&G PAR.

By feeding the photomultiplier tube 30 output into a lock-in amplifier 52 which is synchronized with the narrow bandpass filter interferometer 42 movement (i.e, via the output from the sine wave driver 48 or 49), the lock-in amplifier 52 can sensitively measure a change in the photomultiplier tube 30 signal as a function of the narrow bandpass filter interferometer 42 orientation. Since atomic emission lines are extremely sharp (on the order of 0.001 nm), any atomic emission detected will show a very strong signal dependence on bandpass filter 42 orientation. In addition, the lock-in amplifier 52 effectively eliminates background emission since the background emission is relatively constant over the small range of wavelengths scanned (3 nm) and an emission at a specific wavelength in that range will appear as a relatively sharp spike. Hence, the arrangements shown in FIG. 5 and 6 are capable of detecting small signals on a relatively large, continuous background and can be used to distinguish closely spaced specific lines.

In the past, narrow bandpass filters have been angularly oriented to center the transmission peak on a particular emission line, but in this invention, it is the intentional scanning onto and off of an emission line which makes possible higher sensitivity by baseline subtraction. Since the background light level can sometimes exceed the intensity of an emission line in the case of a trace species, even when a very narrow bandpass filter is used, baseline subtraction provides an important improvement to the use and performance of this technique. Moreover, since the narrow bandpass filter 42 of the present invention is made to scan a broad (3 nm) wavelength range, the problem of having to exactly angularly orient the filter is eliminated. Furthermore, since multiple lines of a given atom may be detected using a scanning filter 42, positive identification and higher selectivity may be achieved than is possible with a fixed position filter.

As described above in conjunction with FIG. 4, sodium ion (Na) fluoresces at the excitation wavelengths of 588.996 nm and 589.593 nm. A 0.2 nm FWHM narrow bandpass filter interferometer 42 can be angle modulated to detect both lines if it is centered at 589.6 nm and the filter 42 is tilted rapidly (5-300 Hz) to scan a 3 nm range of wavelengths. The doublet emission of sodium should clearly be identifiable as the angular position of the narrow bandpass filter 42 is changed with respect to the collimated light.

In one example, starting with the narrow bandpass filter 42 at normal incidence to the collimated light, no sodium emission is transmitted because the filter 42 has been designed to transmit longer wavelengths (590.000 nm) at normal incidence by the manufacturer (Andover Corp.). As the filter 42 angle is changed (angle arbitrarily assigned as +), the 589.593 nm emission is first transmitted with increasing angle and the 588.996 nm emission is transmitted second for detection by the photomultiplier tube 30. Increasing angular displacement in the same direction tunes the filter 42 towards shorter wavelengths so the filter 42 again blocks transmission of either sodium line; however, any wavelength-continuous emission will be transmitted. The filter 42 will then reach its maximum angular displacement and then retrace its movement in the opposite direction towards normal incidence. During this cycle, the two sodium peaks will be detected again, since the filter transmission is determined by the angle of incidence, rather than the direction of motion. After reaching normal incidence, the filter 42 will continue its angular motion (in the − direction with respect to collimated light). Transmission response of the narrow bandpass filter 42 will be identical for the two previous half cycles since the filter transmission is symmetric with respect to positive and negative angular displacement. Because of this, during one sinusoidal period, a single emission line is detected as four peaks and a doublet (such as sodium) is detected as eight individual peaks, or two peaks during each of the four phases of one cycle.

Figure 7:
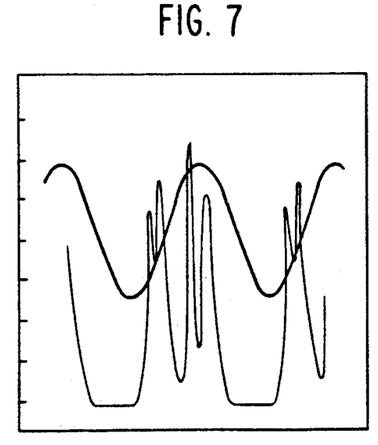
FIG. 7 is an oscilloscope display showing the sodium emission in a $CF_4$ plasma using a narrow bandpass filter tilting at 16 Hertz (Hz)
Figure 8:
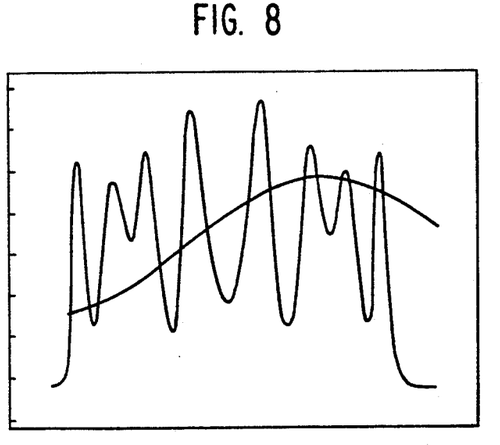
FIG. 8 is an enlarged oscilloscope display showing the sodium emission in a $CF_4$ plasma using a narrow bandpass filter tilting at 16 Hertz (Hz) over a single sine wave period.

FIGS. 7 and 8 show the detected emission signal from a 0.2 nm bandpass filter tilted at 16 Hz, during reactive ion etching of a pyrex substrate in a $CF_4$ plasma. Sodium emission results from the trace presence of sodium tetraborate added to this glass. Over each complete sine wave period in FIG. 7, eight peaks are observed. These eight peaks correspond to four measurements of each of the two sodium emission doublet lines. FIG. 8 shows an enlarged view of data obtained with the angle-tuned narrow bandpass filter over a single sine wave where the eight peaks which are observed provide a reliable identification of sodium emission. Determining the difference between the height of the peaks in FIGS. 7 and 8 and the baseline between periods is one method for subtracting the continuous background emission of the plasma and enhancing sensitivity to sodium detection. Subtraction of the peak height from the baseline may be performed digitally or by using a phase sensitive lock-in amplifier.

Furthermore, it is possible to calibrate the modulated signal against a known intense sodium emission source such as a glass rod in a flame. Since sodium emission of the 588.996 nm line should always be accompanied by emission at 589.593 nm, the measured presence of the doublet can be used to further improve the detection sensitivity of this technique. In this case, background subtraction provides a means for measuring weak emission lines against the background level of the plasma and the high resolution of the technique further improves detection sensitivity and reliability.

In a similar manner to identifying sodium impurities, etch endpoints can be identified by sensing trace copper emissions that would be emitted when the etch process reaches an aluminized line containing copper atoms. Copper emissions are detectable at 522.006 nm and 521.820 nm. By centering a 0.2 nm FWHM narrow bandpass filter at 522.010 nm and angle modulating it through a 3 nm range, both copper emission lines will be observed and the presence of both lines can serve as a confirmation that copper has been detected. Background subtraction is used to provide sensitivity of detection and high resolution is used to provided identity of emission as well as to improve sensitivity since both lines must be observed.

An alternate embodiment of the invention uses a narrow bandpass filter which is alternately positioned in two angles corresponding to a wavelength on the center of a peak, such as sodium, and a wavelength off the emission peak. Instead of smoothly scanning back and forth between the two positions, measurements are recorded at one position for a fixed time increment (with the signal level averaged during this time for an improved signal to noise ratio), then the position is rapidly switched to the alternate setting and similar averaged measurement is made. The background level, corresponding the off-peak position, is subtracted from the signal level measured at the on-peak position. Background subtraction by this approach improves detection sensitivity, but does not provide a spectroscopic verification of the signal identity (i.e., as by the measurement of a doublet).

While the invention has been described in terms of its preferred embodiments where either a Fabry-Perot interferometer 18 or a tiltable narrow bandpass filter interferometer 42 are used to identify trace constituents during a transistor or semiconductor manufacturing process such as during etching or plasma assisted deposition, those skilled in the art will recognize that the invention can be practiced with modification within the spirit and scope of the appended claims.

Having thus described our invention, what we claim as new and desire to secure by Letters Patent is as follows:

1. A system for monitoring a plasma during solid state device manufacturing, comprising:
    means for collecting light from a plasma reactor;
    means for collimating said light from said plasma reactor to form a collimated beam of light;
    an interferometer positioned in the path of said collimated beam of light, said interferometer including a selection means for selectively permitting only certain wavelengths of light in said collimated beam of light to pass through said interferometer and a tiltable bandpass interferometer filter, said selection means includes a means for driving said tiltable bandpass interferometer filter to first and second angular orientations relative to said collimated beam of light, said first and second angular orientations of said bandpass interferometric filter respectively defining a first and second wavelengths of light which pass through the interferometer, said means for driving modulates said tiltable bandpass interferometric filter between said first and said second angular orientations on a periodic cycle, said means for driving includes an audio speaker which emits acoustic waves, said acoustic waves being selectively transmitted from said audio speaker according to the output from an audio driver;
    means for collecting light in said certain wavelengths which pass through said interferometer;
    means for sensing an intensity of said collected light in said certain wavelengths; and
    means for correlating said means for sensing with said selection means.

2. A system for monitoring a plasma during solid state device manufacturing, comprising:
    means for collecting light from a plasma reactor;
    means for collimating said light from said plasma reactor to form a collimated beam of light;
    an interferometer positioned in the path of said collimated beam of light, said interferometer including a selection means for selectively permitting only certain wavelengths of light in said collimated beam of light to pass through said interferometer and a tiltable bandpass interferometer filter, said selection means includes a means for driving said tiltable bandpass interferometer filter to first and second angular orientations relative to said collimated beam of light, said first and second angular orientations of said bandpass interferometric filter respectively defining a first and second wavelengths of light which pass through the interferometer, said means for driving modulates said tiltable bandpass interferometric filter between said first and said second angular orientations on a periodic cycle, said means for driving including a means for dampening the movement of said tiltable bandpass interferometric filter;
    means for collecting light in said certain wavelengths which pass through said interferometer;
    means for sensing an intensity of said collected light in said certain wavelengths; and
    means for correlating said means for sensing with said selection means.

3. A system for monitoring a plasma during solid state device manufacturing, comprising:
    means for collecting light from a plasma reactor;
    means for collimating said light from said plasma reactor to form a collimated beam of light;
    an interferometer positioned in the path of said collimated beam of light, said interferometer including a selection means for selectively permitting only certain wavelengths of light in said collimated beam of light to pass through said interferometer;
    means for collecting light in said certain wavelengths which pass through said interferometer;
    means for sensing an intensity of said collected light in said certain wavelengths;
    means for correlating said means for sensing with said selection means; and
    a means for subtracting background emissions in said plasma reactor sensed by said means for sensing from said intensity of said collected light in said certain wavelengths.

4. A method for monitoring trace constituents during semiconductor processing, comprising the steps of:
    collecting light from a plasma reactor;
    collimating the light collected from said plasma reactor;
    directing the collimated light towards an interferometer;
    controlling said interferometer to selectively permit certain wavelengths of light to pass through said interferometer;
    collecting the light at the certain wavelengths which passes through said interferometer;
    sensing the intensity of light collected at certain wavelengths;
    correlating the sensed intensity with said certain wavelengths of light which pass through said interferometer; and
    subtracting background emissions from said light collected at said certain wavelengths.

5. A method as recited in claim 4 wherein said step of subtracting includes the step of comparing a peak height of said light collected at said certain wavelengths with a baseline emission.

6. A method for monitoring trace constituents during semiconductor processing, comprising the steps of:
    collecting light from a plasma reactor;
    collimating the light collected from said plasma reactor;
    directing the collimated light towards an interferometer;
    controlling said interferometer to selectively permit certain wavelengths of light to pass through said interferometer;
    collecting the light at the certain wavelengths which passes through said interferometer;
    sensing the intensity of light collected at certain wavelengths, said sensing step includes the steps of sensing a first emission intensity at a first wavelength where a particular atomic emission should occur and sensing a second emission intensity at a second wavelength where said particular atomic emission does not occur, and subtracting said second emission intensity from said first emission intensity;

correlating the sensed intensity with said certain wavelengths of light which pass through said interferometer.

* * * * *